(12) United States Patent
Tiemens

(10) Patent No.: US 6,568,395 B2
(45) Date of Patent: May 27, 2003

(54) MULTIPLE EARPLUG ARRANGEMENT

(75) Inventor: Jim Tiemens, Laguna Nigel, CA (US)

(73) Assignee: Bacou-Balloz USA Safety, Inc., San Diego, CA (US)

( * ) Notice: Subject to any disclaimer, the term of this patent is extended or adjusted under 35 U.S.C. 154(b) by 0 days.

(21) Appl. No.: 10/212,283

(22) Filed: Aug. 1, 2002

(65) Prior Publication Data

US 2003/0029458 A1 Feb. 13, 2003

Related U.S. Application Data

(60) Provisional application No. 60/311,440, filed on Aug. 10, 2001, provisional application No. 60/311,441, filed on Aug. 10, 2001, and provisional application No. 60/311,610, filed on Aug. 10, 2001.

(51) Int. Cl.⁷ .............................................. A61F 11/00
(52) U.S. Cl. .................................... 128/864; 128/865
(58) Field of Search ........................... 128/864–868; 221/186, 265; 181/128, 129, 130, 131, 135

(56) References Cited

U.S. PATENT DOCUMENTS

| | | | |
|---|---|---|---|
| D253,723 S | 12/1979 | Leight | |
| 4,434,794 A | 3/1984 | Leight | |
| 4,608,217 A | * 8/1986 | Calki | 128/864 |
| 4,774,938 A | * 10/1988 | Leight | 128/864 |
| 4,806,186 A | * 2/1989 | Sirkin et al. | 128/864 |
| 5,044,463 A | * 9/1991 | Carr | 128/864 |
| 5,188,123 A | 2/1993 | Gardner, Jr. | |
| 5,249,309 A | 10/1993 | Berg et al. | |
| 5,573,015 A | 11/1996 | Williams | |
| 5,799,658 A | 9/1998 | Falco | |
| 5,811,742 A | 9/1998 | Leight | |
| 6,006,857 A | 12/1999 | Leight et al. | |

* cited by examiner

Primary Examiner—Michael A. Brown
(74) Attorney, Agent, or Firm—Leon D. Rosen

(57) ABSTRACT

An earplug arrangement enables low cost manufacture and storage of earplugs and convenient dispensing of individual earplugs. The earplugs are formed from an extrusion of a maximum diameter of about 12 mm and with narrow locations spaced apart by about 1 to 5 cm to separate the extrusion into a chain of at least ten earplugs, where the last earplug of the chain of earplugs formed by the extrusion can be cut from the rest of the chain for insertion into a person's ear canal. The chain of earplugs is stored in a plurality of loops in a container, as in a plurality of loops wrapped about a cylinder. The extrusion can include a stiffening core of stiff first material and an extruded covering of a soft resilient foam second material surrounding the core, the thickness of the second material being less than half as great at the narrowed locations as at maximum diameter locations while the core is of uniform cross-section along the entire length of the extrusion.

17 Claims, 3 Drawing Sheets

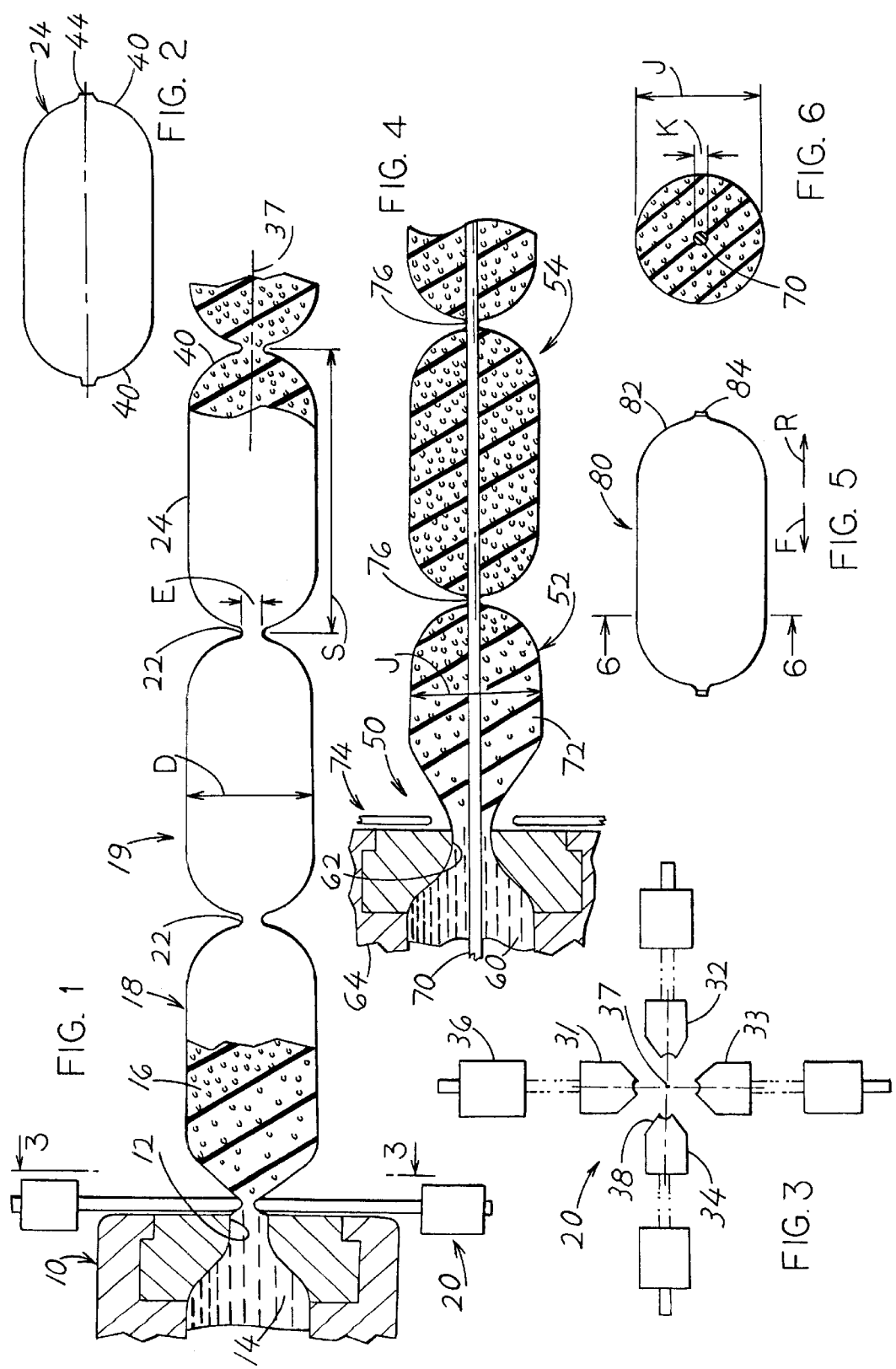

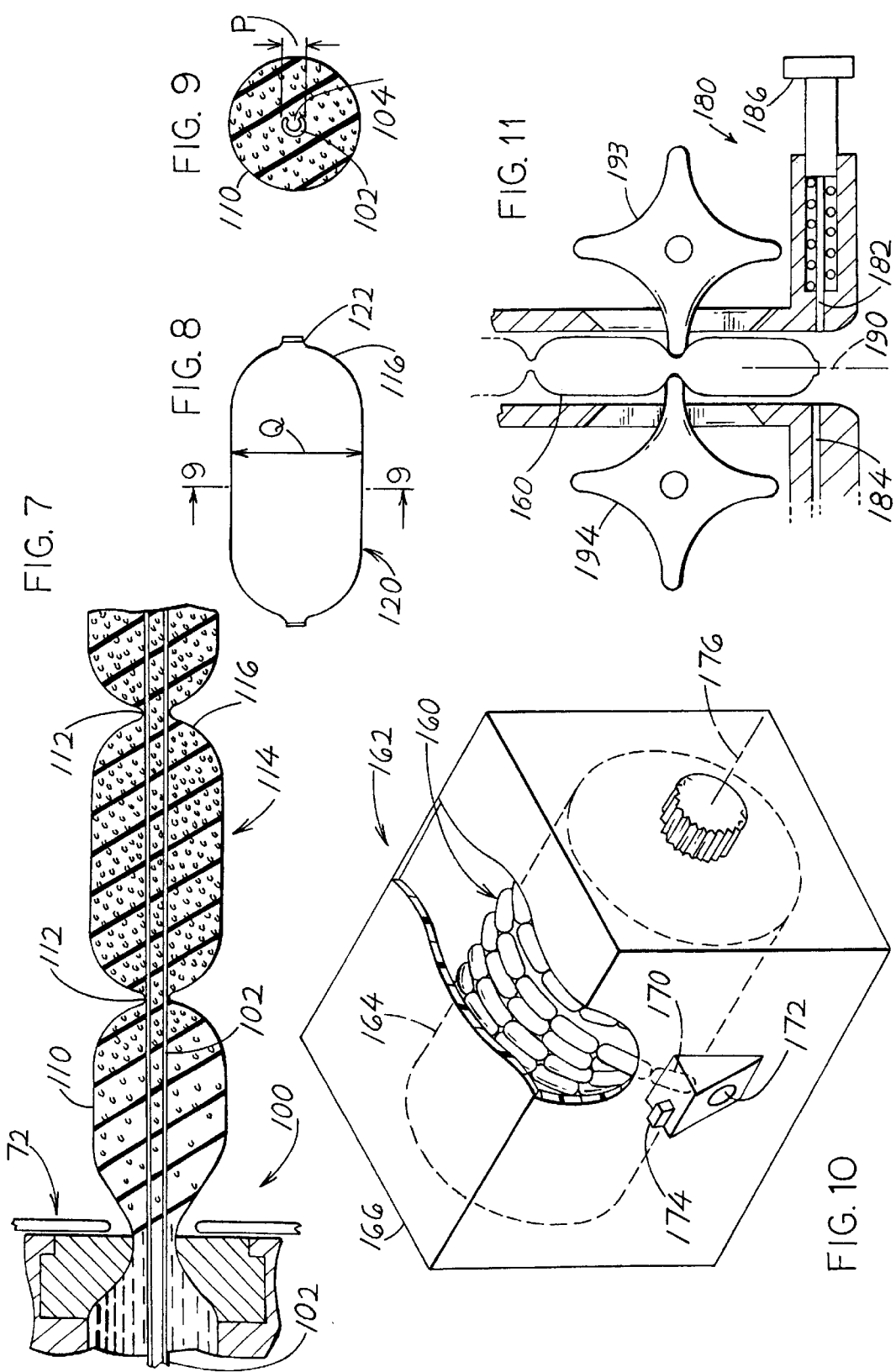

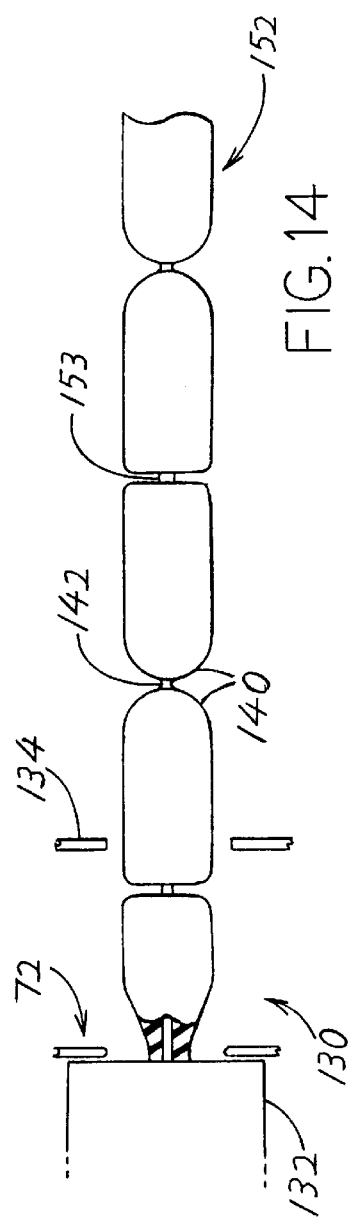
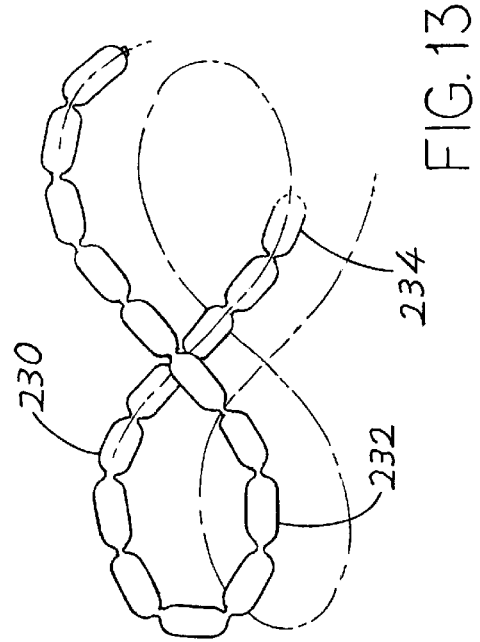
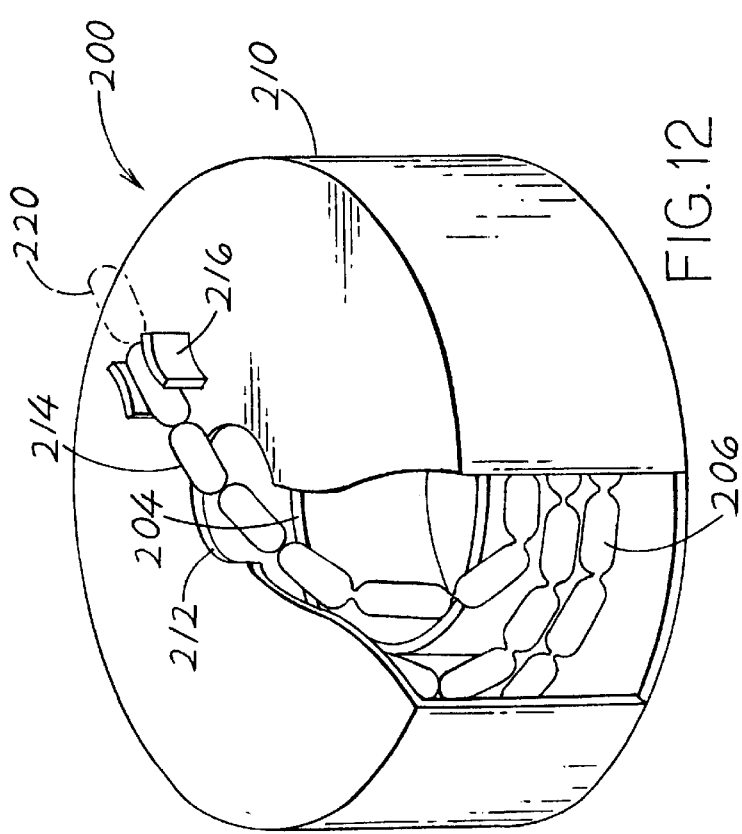

MULTIPLE EARPLUG ARRANGEMENT

CROSS-REFERENCE TO RELATED APPLICATION

Applicant claims priority from Provisional patent applications 60/311,440, 60/311,441, and 60/311,610, all filed Aug. 10, 2001.

BACKGROUND OF THE INVENTION

Earplugs are commonly produced by punching a plug out of a plate of material or molding individual earplugs in individual molds. It is also possible to form earplugs by extruding material that is cut into earplugs. U.S. Pat. No. 5,753,015 describes feeding a small diameter core of round cross-section through an extrusion head while resilient foam material is extruded around the core, to provide a continuous extrusion. As the extrusion cools, it is cut into discrete pieces of about 25 mm length to thereby form individual earplugs. Patent publication WO 02/26465 describes extruding foamable material that will form a slow recovery foam, through an extrusion head, and using a knife blade to cut the extrusion whenever it projects by about 25 mm from the extrusion head, to thereby form individual earplugs. In both cases, the individual earplugs resulting from cutting the extrusion as it emerges from the extrusion head, must be packaged. Earplugs which were very easily packaged and withdrawn from the packaging would be of value.

SUMMARY OF THE INVENTION

In accordance with one embodiment of the present invention, an earplug arrangement and method for forming it are provided, which enables low cost production, storage, shipping, and dispensing. The earplug arrangement includes multiple earplugs connected in series to form a chain of earplugs. The chain of earplugs is formed by an extrusion of foamable material which is stored in a plurality of loops, with individual earplugs obtained by severing the last earplug in the chain from the rest of the chain. During extrusion, locations of minimum diameter are formed at uniform spacings of about 1 cm to 5 cm to define the opposite ends of earplugs. This facilitates bending of the chain to store it in loops or turns, and facilitates severing of the last earplug from the chain.

In one arrangement, the chain include a core of elastomeric material which is at least twice as stiff as the material of the foam covering that was extruded around the core. The core resist column-like collapse when the earplug is pressed into the ear canal. The core also holds the chain together and allows the ends of the earplugs to be of a small diameter less than one-fourth the maximum diameter along the extrusion, to more clearly define the individual earplugs and facilitate cutting of earplugs from the chain.

The novel features of the invention are set forth with particularity in the appended claims. The invention will be best understood from the following description when read in conjunction with the accompanying drawings.

BRIEF DESCRIPTION OF THE DRAWINGS

FIG. 1 is a partial sectional side elevation view showing a process and equipment for producing a chain of earplugs and also showing a portion of such chain of earplugs, where the chain comprises a single material.

FIG. 2 is a side elevation view of one earplug of the chain of FIG. 1, after it has been cut from the chain.

FIG. 3 is a front elevation view of compressing apparatus of FIG. 1, taken on line 3—3 thereof.

FIG. 4 is a sectional side view of a method and equipment for generating a chain of earplugs of another embodiment of the invention, with a core of material that is stiffer than the extruded covering lying around the core, and showing a portion of the chain of earplugs.

FIG. 5 is a side elevation view of one of the earplugs of the chain of FIG. 4, after it has been cut from the chain.

FIG. 6 is a sectional view taken on line 6—6 of FIG. 5.

FIG. 7 is a sectional side view showing a method and equipment for producing a chain of earplugs of another embodiment of the invention, and showing a portion of the chain of earplugs.

FIG. 8 is a side elevation view showing one of the earplugs of the chain of FIG. 7 after it has been severed from the chain.

FIG. 9 is a sectional view taken on line 9—9 of FIG. 8.

FIG. 10 is a partially sectional isometric view showing a holder for holding a chain of earplugs and dispensing them.

FIG. 11 is a sectional view of a portion of the holder of FIG. 10.

FIG. 12 is a partially sectional isometric view of a holder of another embodiment of the invention, with a chain of earplugs therein.

FIG. 13 is an isometric view of a chain of earplugs stored in zig-zag loops.

FIG. 14 is a partially sectional side elevation view showing a method and equipment for constructing a chain of earplugs of another embodiment of the invention, and showing a portion of the chain, wherein only the front ends of the earplugs are rounded.

DESCRIPTION OF THE PREFERRED EMBODIMENTS

FIG. 1 illustrates an extrusion head 10 with an opening 12 through which flowable polymer material 14 is extruded. The polymer material 14 is a foamable material, and after passing out through the opening 12, the material expands in diameter as it foams, until it reaches a maximum diameter D and solidifies to become a resilient solid foam 16. The diameter D is about 12 mm so it can fit snugly into a person's ear canal and block sound. Accordingly, the extrusion 18 is constructed so it can be cut into individual earplugs.

In accordance with the present invention, applicant does not cut the earplugs as they emerge or soon after they emerge from the extrusion head 10, but instead leaves a long extrusion 18 which forms a chain of earplugs 19 for easier storage and dispensing. A compressor 20 is located close to the extrusion head 10 to pinch the extrusion emerging from the opening 12. This leaves locations 22 of minimum diameter E at spacings S of between about 1 cm and 5 cm so individual earplugs 24 between adjacent locations 22 are long enough to be easily inserted into the ear canal and pulled out without excessive waste of material. The compression occurs close to the extrusion head before the extruded material has fully solidified (preferably within 5 cm of the extrusion head), and the compressor does not heat the extrusion.

FIG. 3 shows one form of compressor 20, which includes four compressor elements or dies 31–34 and actuators 36 for moving the compressor elements simultaneously close together toward the extrusion axis 37 to compress the extrusion and then away from the extrusion. This results in the locations 22 of small diameter. The particular compressor elements have sides 38 that abut one another. It is also possible to have compressor elements that overlap one another. The compressor 20 is preferably located close to the extrusion head, where the foamable material has not foamed to its full diameter D. As a result, foamable material on either side of the compression location continues to foam and grow so as result in each earplug 24 having rounded ends 40. The particular foam material 16 is preferably a slow recovery foam material, which can be rolled to a small diameter and inserted into the ear canal, and which resiliently expands over a period such as thirty seconds to fill the ear canal and block it. If a resilient foam of the rapid recovery type, which recovers to its full diameter within one second, is used, then earplugs of such material are difficult to insert into the ear canal unless means are provided to prevent column-like collapse.

FIG. 2 illustrates one earplug 24 which results from a pair of cuts at two locations 22 of the chain of FIG. 1. The earplug has rounded ends 40 and has a small protuberance or nipple 44 at each of its rounded ends where it was cut. The earplugs are not cut from the chain until at least one hour, and usually at least one day, after the extrusion is formed when the chain is of room temperature.

FIG. 4 shows a system 50 for producing an extrusion 52 that forms a chain of earplugs 54 of another embodiment of the invention. As a foamable and flowable material 60 is extruded through an opening 62 of the extrusion head 64, a core 70 of elastomeric material at least twice as stiff as the foam is fed through the extrusion opening 62. The result is the extrusion 52 that includes the core 70 and a covering 72 of resilient polymer foam, the foam material preferably being a fast recovery foam rather than a slow recovery foam. A compressor 74 similar to the compressor 20 of FIG. 3 is provided to create locations of small diameter that are spaced apart by about 1 to 5 cm, and where the extrusion later can be cut to form individual earplugs. The compressor 74 preferably compresses the foamable material to substantially eliminate it at the location 76, so the location 76 consist of only the core 70. In practice, a small amount of the covering material lies around the core at the locations 76. The narrow locations facilitate cutting of earplugs from the chain, and make the chain easy to bend into loops, to turns for storage.

FIG. 5 illustrates one of the earplugs 80 which has been cut from the chain 54 of earplugs of FIG. 4. The earplug has rounded ends 82, except for nipples 84 where the chain was cut at the narrow location 76. FIG. 6 shows that the diameter K of the core 70 is less than half and preferably less than one-quarter the diameter J of the covering. The core 70 is highly useful to prevent column-like collapse as one end, referred to as the front end of the earplug, begins to enter the ear canal as the opposite rear end is pressed forwardly. Without the core 70, it is very difficult to install a resilient foam earplug into the ear canal. In FIG. 6 the core diameter K is about 2 mm, which is no more than one-fourth the earplug maximum diameter D of about 12 mm.

FIG. 7 illustrates a system 100 of another embodiment of the invention, which is similar to that of FIG. 4, except that a core 102 is provided which is in the form of a sleeve. As shown in FIG. 9, the sleeve-shaped core 102 has a gap 104, which is preferably no more than 90°, which allows covering material 110 of resilient fast-recovery foam to flow into the inside of the sleeve 102 to fill it. A compressor 72 similar to compressor 20 of FIG. 3, compresses the covering 110 of resilient foam that surrounds the sleeve 102, at intervals spaced about 1 cm to 5 cm apart. This leaves locations 112 where the chain of earplugs 114 can be bent to form into a loop, where an earplug can be easily severed form the chain, and where the ends 116 of the earplugs are rounded. FIG. 8 shows one of the earplugs 120 of the diameter D, with protrusions or nipples 122 at its opposite ends. FIG. 9 shows that the diameter P of the sleeve is about 3 mm which is less than half and no more than about one-fourth the maximum diameter Q of the earplug.

FIG. 14 illustrates a modified apparatus 130 with a compressor 72 adjacent to the extrusion head 132, and another compressor 134 spaced from the extrusion head. The compressor 72 forms earplug rounded front ends 140 that enter the ear canal, and locations 142 of reduced diameter where the earplugs can be cut. The other compressor 134 is spaced from the extrusion head 132 and forms the rear ends of the earplugs so they are less rounded, but have narrow locations 152 where the earplugs can be severed. The chain of earplugs 152 has alternate minimum diameter locations 142, 152 that are different.

FIG. 10 illustrates a chain of earplugs 160 in a holder 162 which includes a cylindrical drum 164 and a box 166 that surrounds the drum. The drum is rotatably mounted on the box so it can be turned to move the end of the chain at the last earplug 170 of the chain, out through a dispenser opening 172. A cutter 174 which has a blade operated by depressing a handle, cuts earplugs from the end of the chain. The chain of earplugs extends in a plurality of loops, or turns of 360 degrees about the drum axis 176, with considerable bending occurring at the narrowed locations of the chain. The chain of earplugs has a length of at least 50 cm and preferably at least 100 cm, to contain at least ten earplugs and preferably at least 20 earplugs (and more preferably at least 100 earplugs). Each of the turns extending around the drum contains at least five earplugs.

FIG. 11 shows one example of a cutter 180. The cutter includes a pair of blades 182, 184. A handle 186 can be depressed to move the blade 182 beyond the axis 190 of the chain of earplug 192. A mechanism (not shown) moves the other blade 184 simultaneously in the opposite direction across the first blade 182 to shear an earplug between them. A pair of advancing wheels 192, 194 advance the chain of earplugs.

FIG. 12 shows another holder 200 which includes a stationary centerpiece 204 that is preferably in the form of a cylinder or partial cone, and with a chain of earplugs 206 wrapped in a plurality of turns about the centerpiece. A box 210 surrounds the chain of earplugs, and has an opening 212 through which an end portion 214 of the chain can extend. A retainer 216 retains the ends of the chain, and the last earplug 220 of the chain can be cut off at the retainer 216.

FIG. 13 shows still another arrangement, where a chain of earplugs 230 is stored in back-and-forth loops such as 232, 234, each of which may be considered to be a complete turn.

Thus, the invention provides earplugs that can be manufactured and stored in a low cost and efficient manner, and a method for constructing the earplugs. The earplugs are formed as an extrusion of about 12 mm diameter to fit snugly in a human ear canal, and can be stored as by wrapping it in a plurality of loops or turns, and with individual earplugs being dispensed by cutting a length of about 1 cm to 5 cm from the extrusion. The extrusion preferably is formed with locations of reduced diameter spaced by between about 1 cm and 5 cm apart, where the extrusion can be readily cut and which provides increased flexibility to the chain to bend it into a turn. The extrusion is preferably formed by compressing it to form the narrow locations, with the compression occurring close to the extrusion head where the foamable material has not yet completely foamed so ends of the earplugs continue to foam and form rounded ends. It is possible to provide a chain of earplugs without narrowed locations, but at least 50 cm long so it can be cut into at least 10 earplugs. The extrusion can include a core which is a solid core or sleeve (a sleeve preferably has a gap) to stiffen the earplug, and with the thickness of resilient foam covering material that surrounds the core having a reduced thickness less than one-quarter maximum thickness at the locations of minimum diameter. It is possible to have slight compressions between opposite ends of the earplug to stiffen it.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. An earplug arrangement, comprising a plurality of earplugs and a holder that holds said plurality of earplugs, wherein:
    said plurality of earplugs are connected in series to form a chain of at least 20 earplugs connected in series, said chain of earplugs includes an end earplug and a rest of said chain, said end earplug being severable from the rest of the chain.

2. The earplug arrangement described in claim 1 wherein:
    said chain of earplugs has locations of maximum diameter and locations of minimum diameter which are of no more than half the diameter at said locations of maximum diameter, said locations of minimum diameter being spaced apart by between about one and five centimeters and separating said chain into visibly distinct earplugs.

3. The earplug arrangement described in claim 1 wherein:
    said earplugs of said chain are all formed from an extrusion of at least one polymer material, with at least one polymer material extending in a length more than fifty times its maximum diameter along the length of said chain.

4. The earplug arrangement described in claim 1 wherein:
    said chain of earplugs extends in at least one approximately 360° loop.

5. The earplug arrangement described in claim 1 wherein:
    said plurality of earplugs comprises an extrusion of only a single foam polymer material, having a maximum diameter of about 12 mm, and having contractions of a diameter less than half said maximum diameter and spaced apart by about one to five cm along the length of the extrusion.

6. The earplug arrangement described in claim 1 wherein:
    said plurality of earplugs comprises a core of first elastomeric material and a covering of a second foam elastomeric material that primarily surrounds said core, said first material has a rigidity at least twice that of said second material;
    said core is of constant cross-section throughout the length of said chain, and said covering has covering locations of maximum and minimum thickness around said core, said covering locations of minimum thickness having a thickness no more than about one-quarter of said maximum thickness.

7. The earplug arrangement described in claim 6 wherein:
    said core is in the form of a sleeve with a gap it, and said second material fills said sleeve.

8. The earplug arrangement described in claim 1 wherein:
    said chain of earplugs extends in a plurality of turns, and said holder comprises a container that surrounds said turns and that has an opening out of which said chain can be withdrawn.

9. The earplug arrangement described in claim 1 wherein:
    said holder comprises a largely cylindrical drum, and said chain of earplugs is wrapped in a plurality of turns about said drum.

10. The earplug arrangement described in claim 9 wherein:
    said holder includes a box surrounding said drum, said drum being rotatable in said box, said box having an opening through which said chain of earplugs can be withdrawn from said box, and a severing device mounted on said box at said opening for severing an earplug from a rest of said chain of earplugs.

11. An earplug arrangement comprising:
    an extrusion forming a multiplicity of at least twenty earplugs connected in series to form a chain of earplugs, said earplugs having ends spaced apart by about one to five centimeters, each earplug having a location of maximum diameter of about 12 mm and said chain having narrow locations where said earplug ends are connected together and where the cross-section of the extrusion is less than one-quarter the cross-section of said earplug maximum diameter;
    a container;
    said chain of earplugs lying in a plurality of turns in said container.

12. The earplug arrangement described in claim 11 wherein:
    said extrusion includes a core of uniform diameter and formed of a first material, and a covering of a second material that surrounds the core, said first material having at least twice the rigidity of said second material, and said second material having a thickness around said core which is less than half as great at said narrow locations as at locations of said maximum diameter.

13. A method for forming an earplug arrangement, comprising:
    extruding a first polymer into a continuous elongated extrusion having a maximum diameter of about 12 mm;
    shaping said extrusion into narrow locations spaced between about one cm and five cm apart along the length of the extrusion where the extrusion can be easily cut, but leaving said extrusion uncut to thereby form a chain of joined earplugs that later can be cut at the narrow regions to form individual earplugs.

14. The method described in claim 13 wherein said step of extruding includes passing a core of a second material stiffer then said first material in its solidified state through an extrusion head while extruding said first material through said extrusion head around said core, said first material being a flowable foamable material that solidifies into a foam, including:
    compressing the extrusion to substantially said core after the extrusion leaves said extrusion head but is still flowable, and before the foamable material of the extrusion solidifies into a foam.

15. The method described in claim 13 wherein said extrusion has an axis and wherein:
    said step of shaping includes moving each of a plurality of compression dies toward said axis and into said extrusion but to locations short of and spaced from said axis to thereby avoid cutting the extrusion into separate pieces.

16. The method described in claim 13 including:
    cutting a plurality of earplugs from an end portion of said chain of earplugs and from each other, while leaving a majority of the chain intact to thereby create individual earplugs for insertion in a person's ear canals.

17. The method described in claim 13 including:
    wrapping the extrusion that forms a chain of joined earplugs, into a plurality of loops that each contains more five earplugs.

* * * * *